US00PP14336P29

(12) United States Plant Patent
Brown

(10) Patent No.: US PP14,336 P2
(45) Date of Patent: Dec. 2, 2003

(54) DIASCIA PLANT NAMED 'CODIPEIM'

(50) Latin Name: *Diascia×hybrida*
Varietal Denomination: Codipeim

(75) Inventor: Graham Noel Brown, Pennant Hills (AU)

(73) Assignee: NuFlora International Pty. Ltd., Macquarie Fields (AU)

( * ) Notice: Subject to any disclaimer, the term of this patent is extended or adjusted under 35 U.S.C. 154(b) by 0 days.

(21) Appl. No.: 10/259,981

(22) Filed: Sep. 29, 2002

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A new and distinct cultivar of Diascia plant named 'Codipeim', characterized by its compact and upright plant habit; freely branching habit; freely flowering habit; light red-colored flowers with darker red-colored centers; and good temperature tolerance.

1 Drawing Sheet

Botanical classification/cultivar designation: Diascia×hybrida cultivar 'Codipeim'.

BACKGROUND OF THE INVENTION

The present Invention relates to a new and distinct cultivar of Diascia plant, botanically known as Diascia×hybrida, and hereinafter referred to by the cultivar name Codipeim.

The new Diascia is a product of a planned breeding program conducted by the Inventor in Cobbitty, New South Wales, Australia. The objective of the breeding program is to create new compact Diascias with numerous uniquely-colored flowers.

The new Diascia originated from a cross-pollination made by the Inventor in 1999 of the Diascia×hybrida cultivar 'Codiapea', disclosed in U.S. Plant patent application Ser. No. 09/996,383 (now abandoned), as the female, or seed parent, with a proprietary Diascia×hybrida selection identified as X98.3.1, not patented, as the male, or pollen parent. The new Diascia was selected as a single plant from the resulting progeny of the cross-pollination by the Inventor in October, 1999, in a controlled environment in Cobbitty, New South Wales, Australia.

Asexual reproduction of the new cultivar by terminal cuttings taken in a controlled environment in Cobbitty, New South Wales, Australia since October, 1999 has shown that the unique features of this new Diascia are stable and reproduced true to type in successive generations.

SUMMARY OF THE INVENTION

Plants of the cultivar Codipeim have not been observed under all possible environmental conditions. The phenotype may vary somewhat with variations in environment such as temperature and light intensity without, however, any variance in genotype.

The following traits have been repeatedly observed and are determined to be the unique characteristics of 'Codipeim'. These characteristics in combination distinguish 'Codipeim' as a new and distinct cultivar of Diascia:

1. Compact and upright plant habit.
2. Freely branching habit.
3. Freely flowering habit.

4. Light red-colored flowers with darker red-colored centers.
5. Good temperature tolerance.

Plants of the new Diascia are most similar to plants of the female parent, the cultivar Codiapea. Compared to plants of the cultivar Codiapea, plants of the new Diascia have stronger stems and tolerate higher temperatures. Compared to plants of the male parent, the selection X98.3.1, plants of the new Diascia are more upright and differ in flower color as plants of the selection X98.3.1 have coral pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Diascia.

The photograph at the top of the sheet comprises a side perspective view of a typical flowering plant of 'Codipiem' grown in a container.

The photograph at the bottom of the sheet comprises a close-up view of typical leaves and flowers of 'Codipeim'.

DETAILED BOTANICAL DESCRIPTION

The aforementioned photographs and following observations and measurements describe plants grown in Encinitas, Calif., in an outdoor nursery during the winter and spring with day temperatures averaging 24° C., night temperatures ranging from 12 to 19° C., and light levels about 4,000 to 6,000 foot candles. Plants were grown for about 16 weeks in 12.7-cm containers and were pinched one time.

Color references are made to The Royal Horticultural Society Colour Chart, 1995 Edition, except where general terms of ordinary dictionary significance are used.

Botanical classification: Diascia×hybrida cultivar Codipeim.

Parentage:

*Female parent.*—Diascia×hybrida cultivar Codiapea, disclosed in U.S. Plant patent application Ser. No. 09/996,383 (now abandoned).

*Male parent.*—Proprietary Diascia×hybrida selection identified as X98.3.1, not patented.

Propagation:

*Type cutting.*—Terminal vegetative cuttings.

*Time to initiate roots, summer and winter.*—About 10 days at 21° C.

*Time to produce a rooted young plant, summer and winter.*—About 26 days at 21° C.

*Root description.*—Fine, fibrous; white in color.

*Rooting habit.*—Freely branching, dense.

Plant description:

*Form.*—Upright and compact plant habit. Freely branching with lateral branches potentially forming at every node. Moderately vigorous growth habit.

*Plant height.*—About 18 cm.

*Plant diameter.*—About 28 cm.

*Lateral branches.*—Length: About 18 cm. Diameter: About 2 mm. Internode length: About 1 to 3 cm. Texture: Smooth, glabrous. Color: 144B.

*Foliage description.*—Arrangement: Opposite; simple. Quantity per lateral branch: About 17. Length: About 2 cm. Width: About 1.5 cm. Shape: Deltoid. Apex: Acute. Base: Truncate. Margin: Slightly serrate towards the base; entire towards the apex. Texture, upper and lower surfaces: Smooth, glabrous. Venation pattern: Pinnate. Color: Young foliage, upper surface: 144A. Young foliage, lower surface: 146C. Fully expanded foliage, upper surface: 147A. Fully expanded foliage, lower surface: 147C. Venation, upper and lower surfaces: 147B. Petiole length: About 2 mm. Petiole diameter: About 1.5 mm. Petiole color: 144A.

Flower description:

*Flower type and habit.*—Solitary zygomorphic flowers arranged on terminal racemes. Five modified petals fused at base: two upper (banner) petals, two lateral petals, and one larger lower lip petal. Flowers not persistent.

*Quantity.*—Freely flowering; typically about 12 to 20 buds and flowers per lateral branch. Flowers face mostly outward.

*Natural flowering season.*—Plants typically flower during the spring in the Northern Hemisphere; flowering continuous during this period.

*Flower longevity on the plant.*—About four days.

*Fragrance.*—Not detected.

*Inflorescence size.*—Length: About 7 to 10 cm. Width: About 4 cm.

*Flower size.*—Length: About 2 cm. Width: About 2.2 cm. Depth: About 1 cm.

*Flower buds (showing color).*—Length: About 4 mm. Diameter: About 5 mm. Shape: Nearly spherical. Color: 50C.

*Petals.*—Quantity/arrangement: Five modified petals fused at base: two upper (banner) petals, two lateral petals, and one larger lower lip petal. Base of banner petals with concave yellow eyespots; lower surfaces of lateral petals modified into nectar spurs; and lower lip petal convex forming a roughly horizontal insect landing platform. Length: Banner petals: About 8 mm. Lateral petals: About 8 mm. Lower lip petal: About 1.2 cm. Width: Banner petals: About 6 mm. Lateral petals: About 8 mm. Lower lip petal: About 1.4 cm. Lateral petal spur: Length: About 8 mm. Diameter, at petal attachment: About 2 mm. Shape, all petals: Roughly spatulate. Apex, all petals: Rounded. Margin, all petals: Entire. Texture, all petals: Smooth, velvety. Color, all petals: When opening, upper surface: 48A. When opening, lower surface: 48B. Fully opened, upper surface: 48A; towards base, 47A; color does not change or fade with development. Fully opened, lower surface: 48B. Nectar spurs: 47A. Eyespot on banner petals: 12A.

*Sepals.*—Arrangement/appearance: Single whorl of five sepals fused at base; star-shaped. Length: About 2.5 mm. Width: About 1.5 mm. Shape: Narrowly elliptic. Apex: Acute. Margin: Entire. Texture, upper and lower surfaces: Smooth, glabrous. Color: Immature and mature, upper surface: 144A. Immature and mature, lower surface: 144A.

*Peduncles.*—Length: About 3.4 cm. Width: About 2 mm. Angle: Upright to about 15° from vertical. Strength: Moderately strong. Texture: Smooth, glabrous. Color: 144A.

*Pedicels.*—Length: About 1 cm. Width: About 1 mm. Angle: About 45 to 60° from the peduncle. Strength: Moderately strong; slender. Texture: Smooth, glabrous. Color: 144A.

*Reproductive organs.*—Stamens: Quantity per flower: Four. Anther shape: Ovoid. Anther length: Less than 1 mm. Anther color: 12A. Pollen amount: Scarce. Pollen color: 12A. Pistils: Quantity per flower: One. Pistil length: About 4 mm. Style length: About 2 mm. Style color: 145B. Stigma shape: Rounded. Stigma color: 145B. Ovary color: 145A.

*Fruit/seed.*—*Fruit and seed production has not been observed.*

Disease/pest resistance: Plants of the new Diascia have not been noted to be resistant to pathogens or pests common to Diascia.

Temperature tolerance: Plants of the new Diascia have been observed to tolerate temperatures from 0 to 35° C.

I claim:

1. A new and distinct cultivar of Diascia plant named 'Codipeim', as illustrated and described.

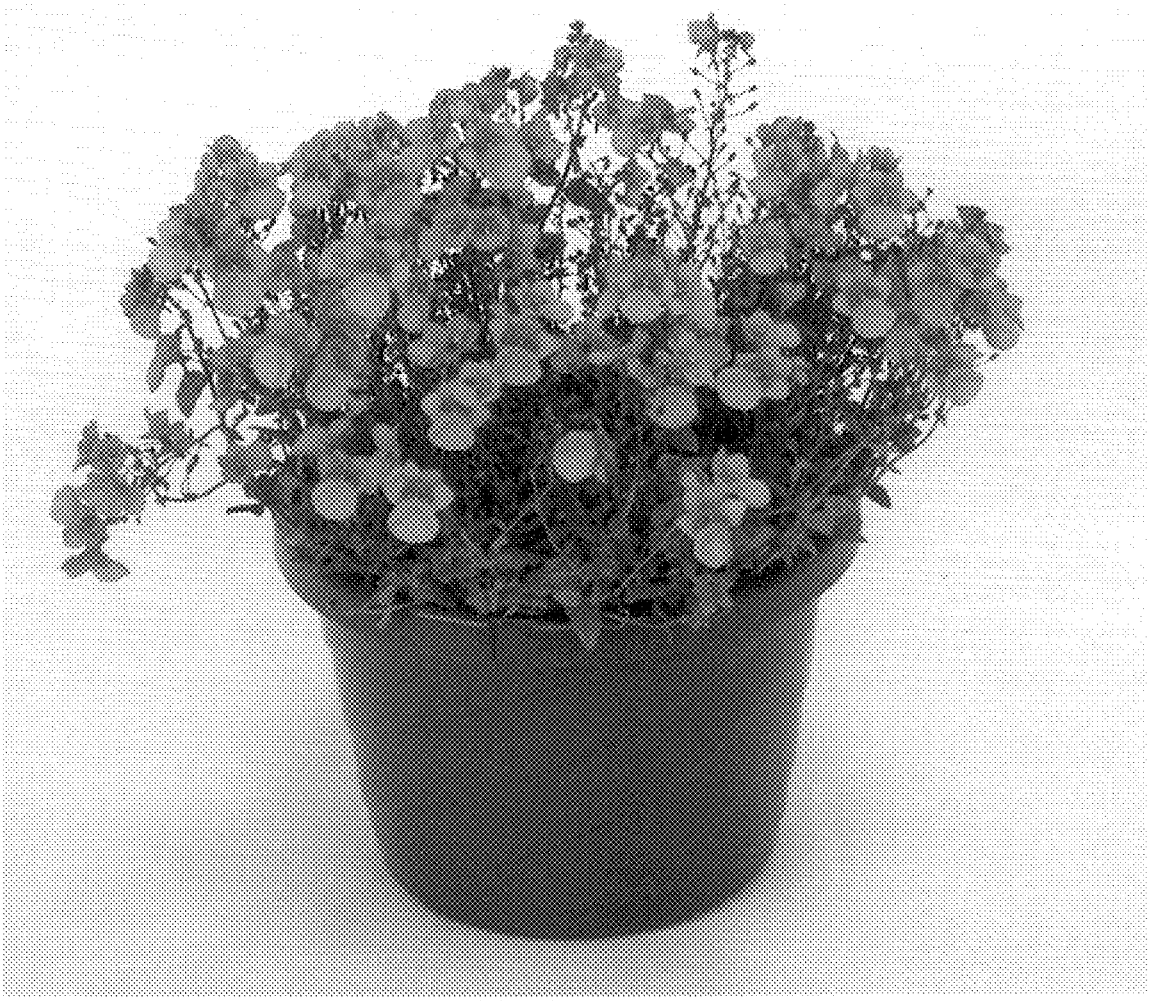
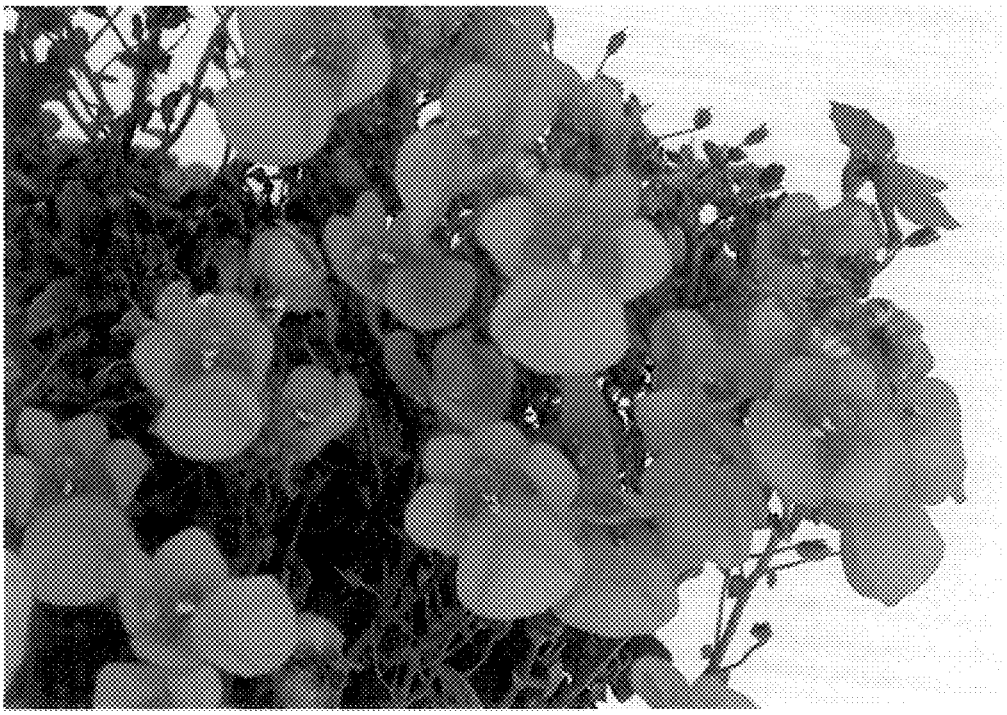

* * * * *